United States Patent [19]

Sarvazyan et al.

[11] Patent Number: 4,947,851
[45] Date of Patent: Aug. 14, 1990

[54] METHOD AND DEVICE FOR ACOUSTIC TESTING OF ELASTICITY OF BIOLOGICAL TISSUES

[75] Inventors: Armen P. Sarvazyan; Viktor Ponomarjev, both of Pushchino, U.S.S.R.; Dusan Vucelic; Goran Popovic, both of Belgrade, Yugoslavia; Akiva Veksler, Pushchino, U.S.S.R.

[73] Assignees: Institute for Physical Chemistry, Belgrade, Yugoslavia; Institute for Biological Physics of the USSR Academy of Science, Moscow, U.S.S.R.

[21] Appl. No.: 234,330
[22] Filed: Aug. 18, 1988

[30] Foreign Application Priority Data
Feb. 19, 1988 [YU] Yugoslavia .............................. 325/88

[51] Int. Cl.$^5$ ................................................. A61B 8/00
[52] U.S. Cl. ................................ 128/660.02; 128/774; 73/597
[58] Field of Search .................... 128/660.02, 739, 774; 7/661.02; 73/597–598

[56] References Cited
U.S. PATENT DOCUMENTS
4,217,912  8/1980  Hubmann et al. ................. 73/574 X
4,250,894  2/1981  Frei et al. ............................ 128/774
4,777,599 10/1988  Dorogi et al. ................... 128/774 X
4,790,188 12/1988  Bussiere et al. ....................... 73/597
4,799,498  1/1989  Collier ................................. 128/774

FOREIGN PATENT DOCUMENTS
1357827 12/1987  U.S.S.R. ................................. 73/597

Primary Examiner—Francis Jaworski
Attorney, Agent, or Firm—Helfgott & Karas

[57] ABSTRACT

In a method and device for the non-invasive acoustic testing of the elasticity of soft biological tissues for the diagnosing of physiological and pathological state in humans and animals, tangential oscillatory deformations of the frequency range of 0.5–30 kHz are excited on the surface of a tissue, and a velocity of the excited surface wave propagating along the vector of the initial displacement is determined. The device includes a probe with one transmitting and two receiving piezotransducers equipped with contact tips and mounted to the body of the probe by elongated shafts which serve as acoustic delay lines, and an electronic device which forms pulses to excite the transmitting transducer, processes the received acoustic signals, measures the time-of-flight of acoustic pulses from the transmitting transducer to the receiving transducers, converts it into the velocity of surface wave and displays the value of the velocity.

6 Claims, 4 Drawing Sheets

METHOD AND DEVICE FOR ACOUSTIC TESTING OF ELASTICITY OF BIOLOGICAL TISSUES

BACKGROUND OF THE INVENTION

The present invention relates to the testing of elastic properties of soft biological tissues. More particularly, the present invention provides an acoustic device and method for noninvasive measurement of the velocity of surface acoustic waves in tissues thus providing the means for estimating the shear elastic properties of tissues for the purposes of medical diagnosis.

The viscoelastic properties of biological tissues are directly related to their structural organization. It was found that bulk elastic properties of tissues are mainly determined by their molecular composition, while shear elasticity is characterized of higher levels of structure. Physiological processes in an organism may result in structural changes in tissues that can be detected by measuring their shear elastic properties.

The methods of testing the viscoelastic properties of tissues are essentially based on invasive measurements on isolated samples. Maxwell, for example, employed torsional vibrations of a sample cut in the form of cylindrical rod fixed at one of the ends (Maxwell B., ASTM Bull, #215, 76, 1956). Shear modulus was determined by measuring the magnitude of force necessary to provide a given deformation at the other end of the rod. The range of working frequencies was 0.001 to 200 kHz.

For measuring the bulk elastic properties, i.e. the ultrasonic velocity and bulk compressibility of media a great variety of methods using bulk acoustic waves in a high-frequency range were developed. For example, according to one of those methods (Nole A. W., Mowry S. C. J. Acoust. Soc. Amer., 20, 432, 1948) the speed of sound was evaluated from the measurement of time-of-flight of an acoustic pulse in the sample being tested which is immersed in a liquid between the ultrasonic transducer and reflector.

Among the known methods of noninvasive testing of bulk elastic properties of tissues is the method and device for noninvasive monitoring the instantaneous fluctuations in viscoelasticity-related properties of a living tissue (Benjamin Gavis, European Patent No. EP 0 135 325 A2, U.S. Pat. No. 4,580,574, T. 1065). The device comprises a pair of substantially parallel spaced-apart piezotransducers, one of them being adjustable with respect to the other to enable insertion and clamping of a segment of a living tissue therebetween. One transducer is connected to a high frequency generator and the other is attached through an amplifier and demodulator to a signal analyzer. The frequency of the ultrasonic resonant oscillations induced in a tissue and their magnitude are characteristic of the viscoelastic properties of the tissue.

The aforementioned method of testing the tissues makes it possible to detect certain physiological processes and particularly the changes in the microcirculation of blood. But since the subject of testing are the bulk elastic properties which may vary in tissues by no more than several percent the accuracy of such a method would not be very high, as compared to the accuracy of the methods using the shear elasticity which may change in some cases by hundreds percent, depending on the physiological state of a tissue. The method does not imply any means to control the force by which the transducers are pressed to a tissue sample placed in the gap therebetween. But such a pressure affects the properties of the samples and still increases the error of measurement. Besides, because it is often difficult to provide access to the tested tissue from the opposite sides, this technique is not applicable to the most of the body.

It is impossible to evaluate by means of this method one of the important characteristics related to the structural organization of living tissues—their anisotropy, i.e. the difference in mechanical properties in various directions.

The possibilities of testing the shear elastic properties of biological tissues were investigated in the paper (V. A. Passechnik, A. P. Sarcazyan: On the possibility of examination of the muscle contracting models by measuring the viscoelastic properties of the contracting muscle—Studia Biophysica, Berlin, Band 13, 1969, Heft 2, s, 143-150). In this work the changes in elastic properties of an isolated muscle during contraction were studied. The low frequency acoustic oscillations (450 to 1200 Hz) were excited in a sample by means of a flexural piezotransducer and received at a distance by the like piezotransducer. The tension of a muscle was measured in various phases of contraction. The modulus of shear elasticity was evaluated by measuring the amplitude and the phase of received signal.

According to the other method of testing the shear elasticity of tissues (R. O. Rotts, D. A. Christman, E. M. Buras: The dynamic mechanical properties of human skin in vivo, J. Biomechanics, Vol. 16 , #6, pp. 365-372, 1983) the shear oscillations in tissue were produced by a "recorder" (a phonograph recording cutterhead) touching the tissue surface with its contact tip (stylus). A phonograph cartridge with a stylus was used as a receiver. Measurements were conducted in the frequency range of 200-1000 Hz.

The recorder was excited by the white noise sound generator; the characteristic frequencies were estimated by means of a spectrum analyzer. The measured parameters were the velocity of propagation of shear waves and their attenuation. The authors of the cited research came to the conclusion that in the low frequency range investigated by said method, the mechanical waves excited in tissues are of shear character and are localized only the superficial layer of the tissue, i.e. in the skin, and because of that only in this range it is possible to provide the selective measurement of skin elasticity, while at higher frequencies the measurement is more difficult because of the small depth of penetration of surface waves. This conclusion is disputable. Since the velocity of shear waves in soft tissues may be 5 to 50 m/s, the wavelength in the frequency range of about 1 kHz should be about 5 to 50 mm. Since the penetration depth of surface waves cannot be much less than a wavelength, the subcutaneous structure elements and in some cases the bone tissue may affect the propagation of the waves of that range, therefore the selectivity of the method as related to measurement in skin seems rather doubtful.

The authors of the said method (R. O. Rotts et al.) do not take into account a peculiarity of surface waves such as the dependence of the velocity and attenuation of a surface wave on the direction of propagation relative to the displacement vector of a tangential oscillation excited by the transmitter on the surface of tissue. Neither was mentioned the anisotropy which is the important feature of shear elasticity in biological tissues (in particular in skin).

The structure of tissues is subject to certain changes in a wide range of clinical situations. The structural changes are closely related to the change in viscoelastic properties of tissues. The bulk elastic properties are not particularly sensitive to the structure and its anisotropy as compared to the shear properties, so the testing of shear properties will prove to be of greater value for clinical medicine and diagnosis. What is therefore needed is a method for noninvasive and highly sensitive testing of shear properties of a tissue along the chosen direction.

DETAILED DESCRIPTION OF THE PREFERRED EMBODIMENTS

Figure 1:
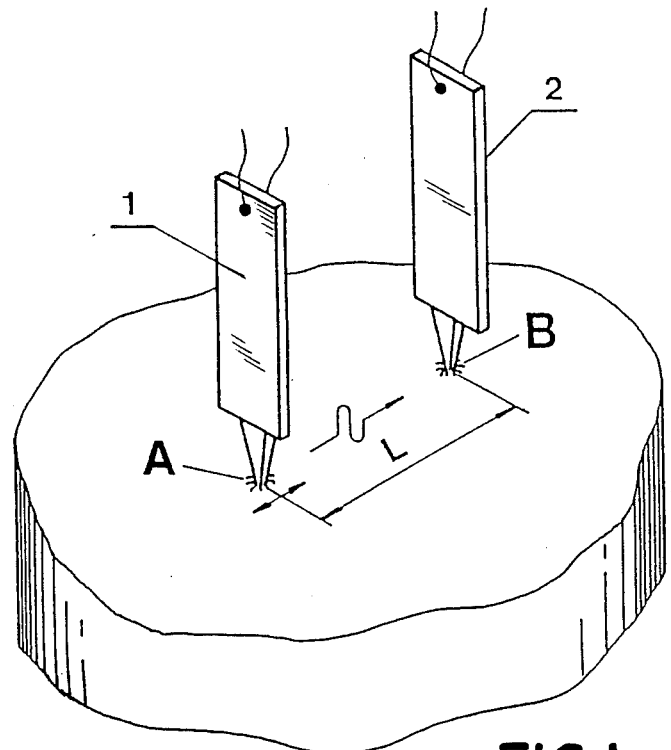
FIG. 1 is an illustration to the principle of the method according to the invention.

The general idea of the method is the following: the transmitting and receiving flexural bimorphous piezotransducers having the contact tips on their ends are brought into mechanical contact with the matter being investigated. Providing an electrical pulse to the transmitter excites a damped tangential oscillation in the matter close to the contact tip of the transmitter, with a frequency in the range of 0.5 to 30 kHz, depending on the construction of the transducer and the properties of the matter. The propagating mechanical oscillation excites an electric signal in the receiver. The velocity of propagation is determined by measuring the time required for a pulse of tangential deformation to travel the distance between the transmitter and the receiver. The velocity and attenuation of a shear wave depends on the angle between the direction of propagation and the vector of displacement of the tangential oscillations excited by the transmitter. The wave propagating along the vector of displacement has the maximum velocity and the minimum attenuation. This is the reason for placing the transmitter and receiver as shown in FIG. 1, with 1 and 2 are the transmitting and receiving flexural bimorphous piezotransducers; The vector of displacement in both the transducer coincides with the line connecting the contact tips A and B.

Figure 3:
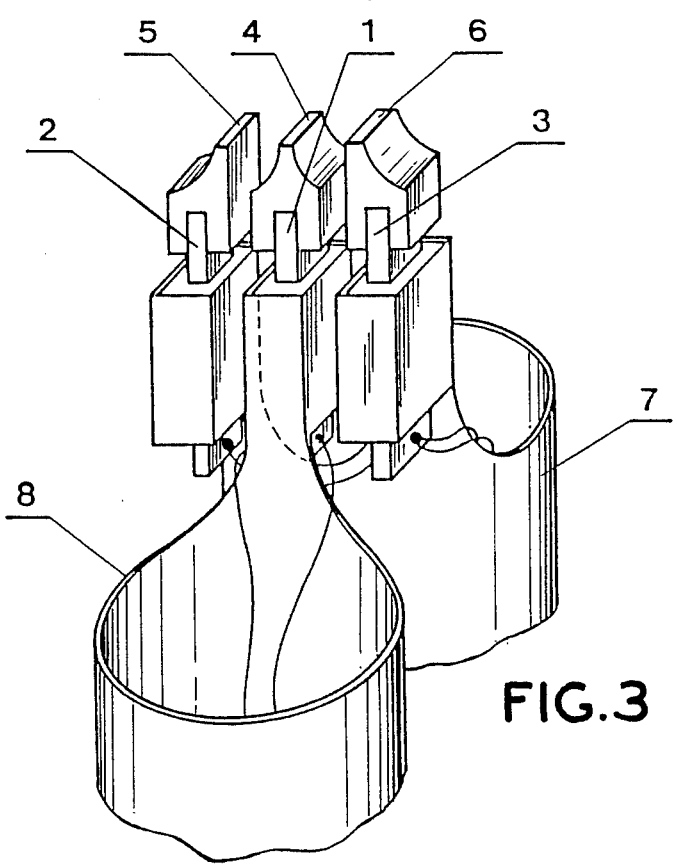
FIG. 3 shows the arrangement of the transducers with their contact tips.
Figure 2A:
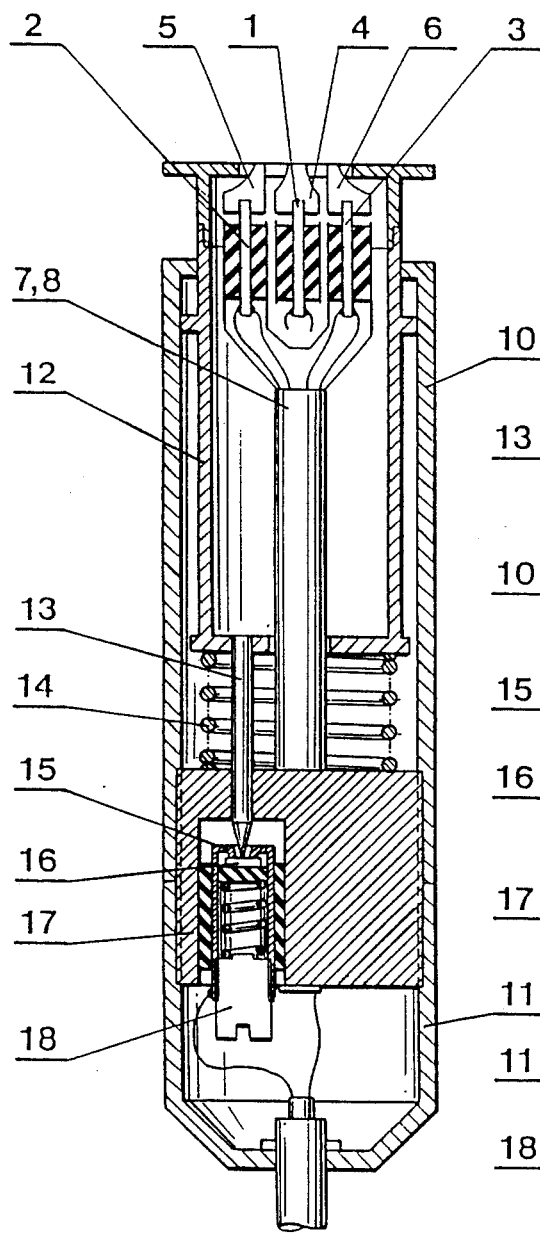
FIG. 2a is a cross-sectional view of the probe.

In the preferred embodiment, the device for measuring the velocity comprises a probe with one transmitting and two receiving piezotransducers, the receiving transducers being placed symmetrically with respect to the transmitter as shown in FIGS. 2a and 3. Using two receivers instead of single one allows for the differential amplification of the received acoustic signals; this is important because the signal felt by the receiver is small.

Figure 2B:
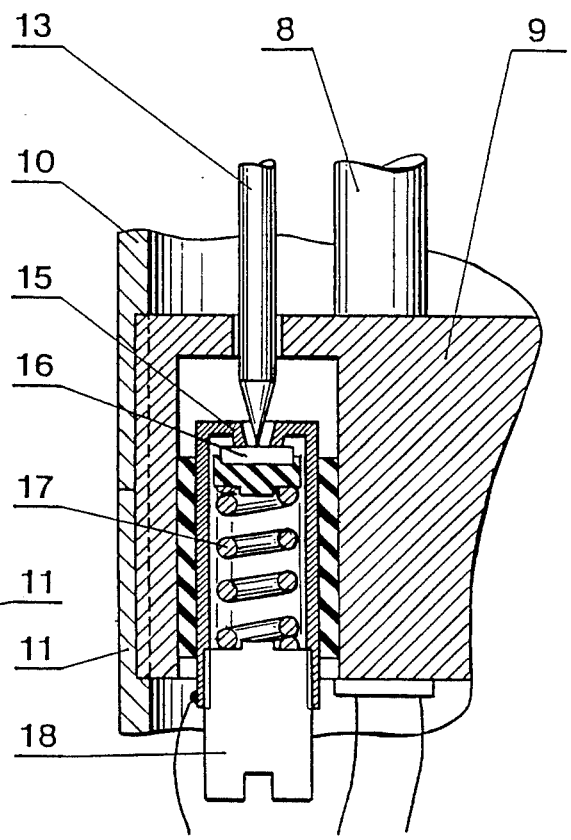
FIG. 2b shows a unit of FIG. 2a for standardizing a force by which the probe is pressed to a tissue.

The three piezotransducers 1, 2, 3 with contact tips 4, 5, 6 are mounted onto the probe as shown in FIGS. 3 and 2a by means of acoustic delay lines 7 and 8 in the form of hollow thin-wall metallic shafts. The length of the shafts is great enough to delay the acoustic signal passing from transmitter to receiver through the body of the probe for a time several times greater than the propagation time in the intended media. The transducers 1, 2, 3, are fixed in the shafts 7 and 8 by means of damping elastic gaskets, all together being placed inside a protective case 12 which serves at the same time as a pressure sensor for standardizing the force by which the probe is pressed to the matter. The case 12 drives the three-state switch (FIG. 2b) comprising a needle contact 13, a spring 14, an immobile tubular contact 15 fixed through insulator plastic gasket in an base 19, an mobile contact plate 16, normally pressed to the contact 15 by a spring 17 separated by an insulator plate.

The switch is normally open. During the operation, it may be switched on only in the case where the force compressing the spring 17, i.e. the force by which the probe is pressed against the matter, is great enough to make the needle 13 touch the plate 16 but still is not so great as to break the contact between the plate 16 and the tubular contact 15. According to said hereabove, the lower limit of force is determined by the spring 14 which is adjusted by displacing the threaded base 9 inside the exterior case 10, while the upper limit of the force is adjusted by the spring 17 which is compressed by a screw 18. The admitted range of the force may be made almost as small as the hysteresis of friction inside the contact unit. It must be large enough though, so as to be easily controlled by hand.

The case 12 and the transducers are arranged so that in the admitted range of force, the contact tips 4, 5 nd 6 occupy a fixed position close to the plane of the working edge of the probe.

Figure 4A:
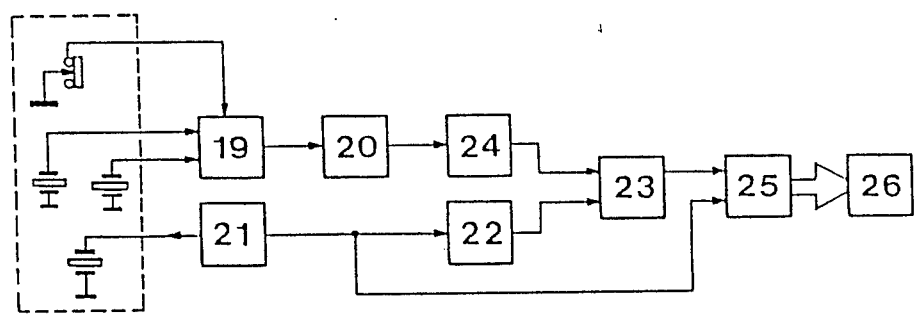
FIG. 4 shows circuit block diagrams.
Figure 5:
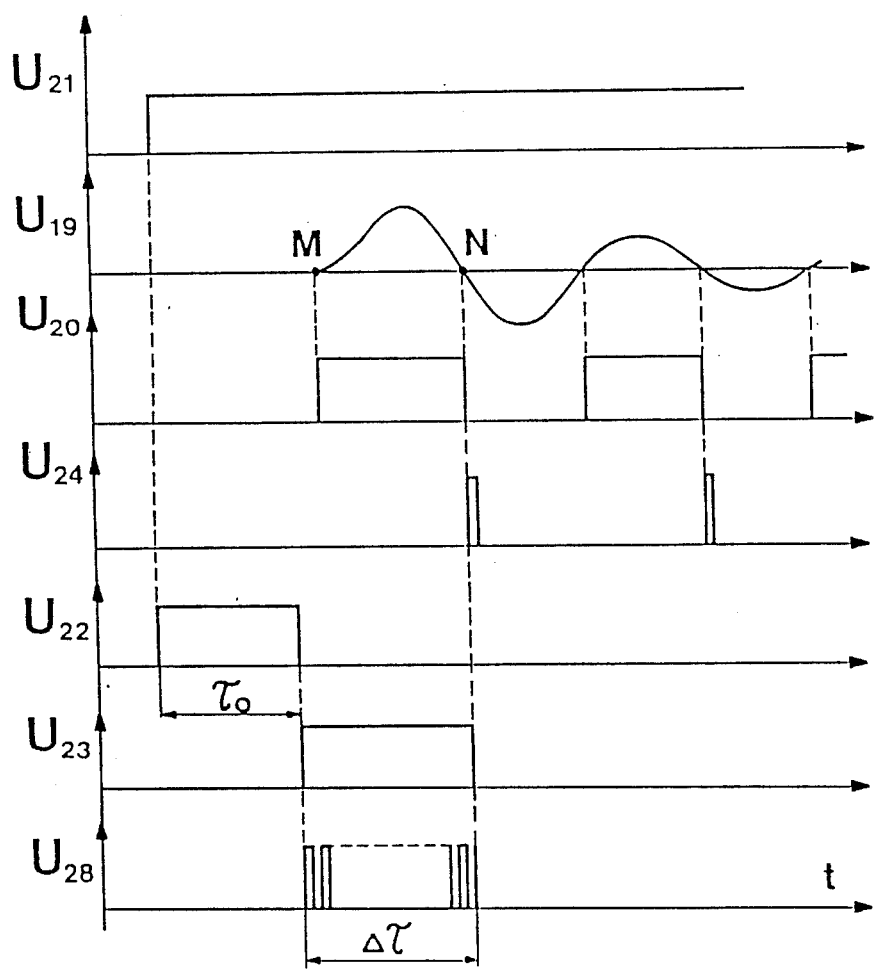
FIG. 5 is the clock diagram of the basic measurement cycle.

The switch enables the operation of the electronic block (see FIG. 4a) comprising a differential input amplifier 19, the chip 20, a bistable (type 74121) circuit 24, a flip-flop circuit 23 a pulse generator 21, delay unit 22, a processing unit 25 and a display unit 26. The pulse generator 21 provides the pulses exciting a flexural deformation in the transmitting piezotransducer; a 30 ms pause between the pulses comprises the elementary measurement cycle (see FIG. 5). When all the tips of the probe are brought into a contact with the matter being tested, the two counterphase electric signals induced in the receivers are sensed at the inputs of the differential amplifier 19. At the same time, the pulse from the generator 21 via the calibrating delay unit 22 sets the flip-flop circuit 23 which gates the count in the processing unit 25. The output of the amplifier 19 is limited by the chip 20 so as to form the pulses with abrupt edges as shown in FIG. 5. The leading edge of the first pulse corresponds to the front of the acoustic wave being first detected by the receiver (event M in FIG. 5), and the trailing edge corresponds to the wave's first passing the zero (unexcited) level (event N). Since the front of an acoustic wave is very smooth and difficult to be detected with enough confidence, the event N is used instead to measure the time-of-flight of the acoustic pulse between the transmitter and the receiver. The trailing edge of the pulse U20 associated with that event resets the flip-flop circuit 23 via the bistable circuit 24 thus disabling the count in the processing unit 25.

Figure 4B:
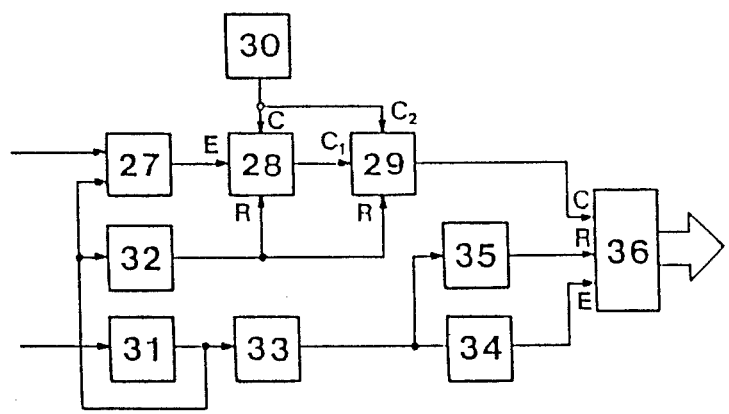
Figure 4C:
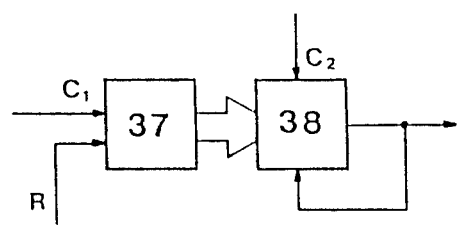

The processing unit 25 is shown in FIG. 4b. It performs the averaging of several measurements of time-of-flight of acoustic pulses and converting the average time into velocity of pulses. It consists of a frequency divider 28 gated through an AND latch 27 by a counter of samples 31, a time/velocity converter 29, a clock generator 30, a counter 36, bistables 32 and 35 and a NOT gate element 33. The possible implementation of the convertor unit 29 is shown in FIG. 4c.

The frequency divider 28 together with counter 37 accumulate the total number of clock pulses during several sampling periods; the divider 28 divides that number by the number of samples. The cycle of the counter 31 is twice the number of samples; during the first half of a cycle its output is HIGH, thus enabling (via latch 27) the sampling is counters 28 and 37. When the output of counter 31 goes LOW, the sampling stops with the average value of time being stored in counter 37. At the sane time, the output of the invertor 33 goes HIGH thus enabling the count in the buffer counter 36 for a certain period measured by a timer 34. The 36 counts the output of the presettable subtracting counter 38 which runs permanently loading the value from counter 37 each time its count goes down to zero, thus providing the pulses with the frequency being the inverse value of the value of time stored in 37. The timer 34 gates those pulses to the counter 36; it is adjustable to provide the means, together with the adjustable delay unit 22, for calibrating the velocity of pulses. The value of velocity accumulated in counter 36 is displayed by the display unit 26. At the end of sampling/display cycle the output of 31 again goes HIGH thus resetting via bistables 32 and 35 the counters 28, 37, 36 and enabling the sampling via latch 27.

According to the present invention the prototype was made to demonstrate the possibilities of the proposed method in different experiments. In Table 1 one can see how the velocity of surface wave may vary over the skin of a human body.

TABLE 1

| The velocity of shear wave, m/s | | | | |
|---|---|---|---|---|
| Forehead | Cheek | Chest | Tip of finger | Skin |
| 28 ± 5 | 20 ± 3 | 21 ± 5 | 60 ± 10 | 35 ± 8 |

Another example is the measurement of the elasticity of human skin before and after the cryomassage. In a group of women chosen by a cosmetologist as having specifically thin skin on their faces the velocity of surface wave measured before the cryomassage was in the range of 20.2 m/s. Immediately after the cryomassage the velocity was in the range of 60 m/s; it returned to the initial value in about 10 minutes. The rate of relaxation of the elasticity of skin after the cryomassage was shown to be specific for the particular type of skin.

One more example is the study of shear elasticity of muscle during contraction. In the isolated resting frog muscle, the velocity of propagation of shear wave along the fibers was about 10 m/s. During contraction it reached 35 m/s. The range of variance of shear wave velocity in the same biological tissue often exceeds 100 percent, while in the case of bulk elastic waves the change is measured by several percent.

It can be seen that the present invention provides the means for testing the tissues, highly sensitive to both the type of tissue and its physiological state, which may be extremely valuable in medical diagnosis, e.g. in diagnosing the skin pathology or in differentiation of normal and pathological tissues during surgical operations.

The experiments also showed that some features of the preferred embodiment prove to be advantageous and even necessary. Particularly, it should be mentioned that because of variety of reasons the force by which the probe is pressed to a tissue impacts to the mechanical state of tissue and strongly affects the results of measurement. The proposed feature of limiting the force makes this error nearly constant and allows it to be taken into account while calibration.

The other important feature is the use of two receivers instead of single one. Besides the fact that it increases the sensitivity it is used to reduce the error that may occur during the manual application of the probe due to occasional shifts in relative position of the transmitting and the two receiving transducers since, it should be considered, the shafts carrying the transducers serve at the same time as acoustic delay lines and thus they must be essentially flexible. The maximum error occurs when the transmitter shifts towards one of the receivers; in this case, the signal comes to that receiver a little earlier than is expected, and same signal comes to the other receiver as later. The receipt of the signals is detected by their first passing the zero; provided the shift is small, the zero of the sum of the delayed signal and the signal that comes in advance only slightly shifts from expected. This shift can be roughly estimated in the following way:

$$A \sin(\omega t + \Psi) = A_1 \sin(\omega t + \psi) + A \sin(\omega t - \psi) \tag{4}$$

where:
A is the amplitude of the resulting signals;
$A_1$ and $A_2$ are the amplitudes of the signals in the receivers;
$\Psi$ is the phase shift of the resulting signal, which occurs due to non-symmetrical position of receiving contact tips,
$\pm \psi$ are the phase shifts of summed signals.

We can rewrite equation (4) in the following way:

$$A \sin(\omega t + \Psi) = A_1 \sin \left| \omega t + \arctg\left(\frac{A_1 A_2}{A_1 + A_2}\right) tg\psi \right| \tag{5}$$

In the small range of displacement of the transmitter with respect to the center position between the receivers, the amplitude of the received signal may be considered as a linear function of the distance and, therefore, we can rewrite equation (5) as:

$$\sin(\omega t + \Psi) \approx \sin \left| \omega t + \arc tg_0\left(\frac{\Delta R}{R} tg\psi\right) \right| \tag{6}$$

where: $R_o$ is half the distance between the contact tips of the receiving piezotransducers, $\Delta R = L - R_o$ is the displacement of the transmitter relative to the contact tips of the receivers of the transmitter relative to the contact tips of the receiver.

Assuming f=5 kHz, $R_o$=3 mm, c=40 m sec$^{-1}$ $\Delta R$=0.3 mm, where fi is the working frequency and c is an average value of the velocity of surface waves in the human skin, taking into consideration the said parameters (6) one can rewrite equation (6) as follows:

$$\sin(\omega t + \Psi) \approx \sin\left(\omega t + \frac{\Delta R}{R} \cdot \psi\right) \tag{7}$$

It can be seen that by using two receiving piezotransducers instead of one, the error which occurs due to changes of the distance between contact tips of the transmitting and the receiving piezotransducers, is decreased approximately ($\Delta R/R$) times, i.e., for the parameters given above the error for double-receiver device is ten times smaller than for one-receiver version of the device.

One more advantage of the preferred embodiment is that the probe can be applied to a surface of tissue all over the body, without clamping it between the transducers or fixing in any other way.

We claim:

1. A method for non-invasive acoustic testing of elasticity of soft biological tissues by transmitting and receiving acoustic waves, comprising the steps of:

providing a probe including one transmitting flexural bimorphous transducers and two receiving flexural bimorphous piezotransducers all having contact tips and mounted to a body of said probe so that vectors of displacement of flexural oscillations in the transmitting and receiving piezotransducers have a direction which coincides with a line connecting the contact tips of said piezotransducers;

applying said probe to a tissue being tested so that said contact tips of said piezotransducers are pressed against said tissue with a standardized force adjusted in said probe within a predetermined range;

exciting a pulse of tangential deformation on a surface of said tissue by said transmitting piezotransducer;

detecting a surface wave propagating in the tissue from the transmitting piezotransducer to the receiving piezotransducers;

determining the time elapsed between the transmitting and receipt of an acoustic pulse travelling across the surface of the tissue; and converting a value of the elapsed time determined into a value of a velocity of the surface wave.

2. The method as claimed in claim 1, wherein said step of determination of the elapsed time between the transmitting and receipt of the acoustic pulse starts at the moment when as a result of a tangential displacement, the tissue being in contact with the transmitting transducer first returns to its unexcited level and stops at the moment when a signal induced in the receiving transmitters first returns to zero.

3. A device for non-invasive testing of elasticity of soft biological tissues, comprising:

a probe to be applied to a tissue being tested and including one transmitting and two receiving flexural bimorphous piezotransducers provided with contact tips and mounted by elongated shafts serving as delay lines to a body of the probe so that the vectors of displacement of flexural oscillations in the one transmitting and the two receiving piezotransducers have a direction which coincides with a line connecting said contact tips, and a unit for standardizing a force by which the piezotransducers are pressed to the tissue being tested; and circuit means connected to said piezotransducers and said pressure standardizing unit to determine a time-of-flight of acoustic pulses passing through the tissue from the transmitting piezotransducer to the receiving piezotransducers, which is indicative of the elasticity of said tissue.

4. The device of claim 3, where the contact tips of the receiving transducers are rigidly mounted in said probe.

5. The device as claimed in claim 3, wherein said pressure standardizing unit includes a hollow case substantially covering the piezotransducers, said casing having an opening on its outer edge through which a tissue being tested is accessed by said piezotransducers, a first spring supporting said case, and a three-state electric switch driven by said case and including an immobile contact fixed to a body of said probe and two mobile contacts, one of said mobile contacts being mounted to the case and another mobile contact being held in contact with said immobile contact by means of a second spring to provide that a force applied to the outer edge of said case is within a predetermined range, the first spring supporting the case being sufficiently compressed to put the mobile contact mounted to the case in contact with another mobile contact held in contact with the immobile contact by said second spring which is adjusted so as to break a circuit between said another mobile contact and the immobile contact if the force exceeds an upper predetermined limit, wherein when the force is beyond a lower predetermined limit in said range the first spring supporting the case is not sufficiently compressed to allow the mobile contact mounted to the case to reach said another mobile contact.

6. The device as claimed in claim 3, wherein said circuit means includes means for converting a value of the time elapsed between the transmitting and receipt of acoustic pulses into velocity of said pulse, and display means to display a value of the velocity.

* * * * *